US012622887B2

(12) United States Patent
Castellano et al.

(10) Patent No.: US 12,622,887 B2
(45) Date of Patent: May 12, 2026

(54) LIQUID PHARMACEUTICAL COMPOSITIONS COMPRISING CITRATE AND CARNITINE

(71) Applicants: IPERBOREAL PHARMA SRL, Pescara (IT); Giuseppe Castellano, Gravina in Puglia (IT); PUERAPULIAE INVEST SRL, Bari (IT)

(72) Inventors: Giuseppe Castellano, Gravina in Puglia (IT); Rossana Franzin, Bitonto (IT); Alessandra Stasi, Molfetta (IT); Fabio Sallustio, Bisceglie (IT); Arduino Arduini, Arogno (CH)

(73) Assignees: Giuseppe Castellano, Gravina in Puglia (IT); IPERBOREAL PHARMA SRL, Pescara (IT); PUERAPULIAE INVEST SRL, Bari (IT)

( * ) Notice: Subject to any disclaimer, the term of this patent is extended or adjusted under 35 U.S.C. 154(b) by 1205 days.

(21) Appl. No.: 17/613,390

(22) PCT Filed: May 14, 2020

(86) PCT No.: PCT/EP2020/063454
§ 371 (c)(1),
(2) Date: Nov. 22, 2021

(87) PCT Pub. No.: WO2020/239459
PCT Pub. Date: Dec. 3, 2020

(65) Prior Publication Data
US 2022/0241235 A1     Aug. 4, 2022

(30) Foreign Application Priority Data
May 29, 2019     (IT) ........................ 102019000007446

(51) Int. Cl.
| | |
|---|---|
| *A61K 31/205* | (2006.01) |
| *A01N 1/126* | (2025.01) |
| *A61K 31/194* | (2006.01) |
| *A61K 47/26* | (2006.01) |
| *A61P 9/10* | (2006.01) |

(52) U.S. Cl.
CPC ............ *A61K 31/205* (2013.01); *A01N 1/126* (2025.01); *A61K 31/194* (2013.01); *A61K 47/26* (2013.01); *A61P 9/10* (2018.01)

(58) Field of Classification Search
CPC ................................................ A61K 31/205
See application file for complete search history.

(56) References Cited

U.S. PATENT DOCUMENTS

| | | | |
|---|---|---|---|
| 8,957,048 B2 * | 2/2015 | Vehige | A61K 36/47 514/57 |
| 9,861,095 B2 | 1/2018 | Dutheil et al. | |
| 2012/0172314 A1 | 7/2012 | Koeffler et al. | |
| 2012/0232024 A1 | 9/2012 | Breyer et al. | |
| 2012/0258087 A1 * | 10/2012 | Jedlinski | A23L 33/175 424/94.1 |
| 2013/0122091 A1 * | 5/2013 | Gennero | A61P 43/00 514/44 R |
| 2016/0302406 A1 | 10/2016 | Young | |
| 2017/0202210 A1 | 7/2017 | Tanaka et al. | |
| 2017/0265456 A1 | 9/2017 | Zhang et al. | |
| 2017/0326100 A1 | 11/2017 | Kang et al. | |
| 2018/0037868 A1 | 2/2018 | Guenther et al. | |
| 2018/0070582 A1 | 3/2018 | Doorschodt | |
| 2018/0289306 A1 | 10/2018 | Toro-Cabrera et al. | |

FOREIGN PATENT DOCUMENTS

| | | |
|---|---|---|
| CA | 3025461 A1 | 12/2017 |
| CN | 102961739 A | 3/2013 |
| CN | 104826164 A | 8/2015 |
| CN | 105838661 A | 8/2016 |
| CN | 106035316 A | 10/2016 |
| CN | 106342787 A | 1/2017 |
| CN | 107148215 A | 9/2017 |
| CN | 107438423 A | 12/2017 |
| CN | 109549032 A | 4/2019 |
| IL | 201880 A | 4/2015 |
| JP | 2001072607 A | 3/2001 |
| JP | 2017057184 A | 3/2017 |
| JP | 2017061531 A | 3/2017 |
| JP | 2017186295 A | 10/2017 |
| KR | 20170111384 A | 10/2017 |
| WO | 02102149 A1 | 12/2002 |
| WO | 2015152429 A1 | 4/2015 |
| WO | 2018098375 A1 | 5/2018 |

OTHER PUBLICATIONS

Rene Hany Tolba: "Improved Preservation of Warm Ischemia-Damaged Porcine Kidneys after Cold Storage in Ecosol, a Novel Preservation Solution", Annals of Transplantation, vol. 20, Jan. 1, 2015, pp. 233-242, table 1.

* cited by examiner

*Primary Examiner* — Gina C Justice
(74) *Attorney, Agent, or Firm* — Gregory P. Einhorn; Greer, Burns & Crain, Ltd.

(57) ABSTRACT

A composition comprising citrate and carnitine which activates the production of the protein Klotho by renal tubule cells protecting them, thus reducing the oxidative stress conditions thereof, which can be used for the conservation, perfusion and reperfusion of organs for organ transplants is disclosed. Furthermore, the composition in the liquid and dietary/nutraceutical formulation can be used for reducing the nephrotoxicity induced by iodinated contrast means, antibiotics, NSAIDs 10 or agents that induce oxidative stress.

16 Claims, 6 Drawing Sheets

Pre-treatment 12h + 6h Iodixanol

Pre-treatment 12h + 6h Gentamycin Sulphate

* p<0.05 vs basal

φ p<0.001 vs H2O2 0.5 mM

LIQUID PHARMACEUTICAL COMPOSITIONS COMPRISING CITRATE AND CARNITINE

FIELD OF THE INVENTION

The present invention relates to the sector of pharmaceuticals and more in particular a composition comprising citrate and carnitine which is able to activate the production of the protein Klotho by the renal cells and therefore is able to reduce damage due to oxidative stress because of exogenous and endogenous causes which can affect the kidneys. The formulation can be used to reduce the nephrotoxicity induced by iodinated contrast media, antibiotics or NSAIDs and by agents that induce oxidative stress. Within the context of the organ transplant sector, the composition can be effectively used for the preservation, perfusion and reperfusion of organs for transplant and for preventing early renal ageing.

BACKGROUND

Klotho protein exists in three different isoforms: α, β e γ. In humans, Klotho α is codified by the gene KL and codifies for an enzyme belonging to the beta-glucosidase family mainly expressed in the distal tubule of the kidney but also at the choroid plexus level of the encephalus, in the parathyroid glands, in the bladder, in the skeletal muscle, in the placenta, in the thyroid gland and in the endothelial cells of the aorta and of the renal artery. (Donate-Correa J, Expression of FGF23/KLOTHO system in human vascular tissue. Int J Cardiol. 2013; Lim K, Vascular Klotho deficiency potentiates the development of human artery calcification and mediates resistance to fibroblast growth factor 23. Circulation. 2012, Lim K, α-Klotho Expression in Human Tissues. J Clin Endocrinol Metab. 2015).

Klotho α, simply known as Klotho, is a protein that contrasts ageing and inflammation; its soluble form mainly released by the kidney is secreted into the blood and performs a protective function throughout the whole organism, in particular at cardiovascular and central nervous system level. In particular, the soluble form α Klotho reduces calcifications in the arteries, protects the heart from hypertrophy (Xie J, Cardioprotection by Klotho through downregulation of TRPC6 channels in the mouse heart. Nat Commun. 2012) through the inhibition of endothelial dysfunction and oxidative stress on the smooth muscle cells (Mencke R, Hillebrands J L; The role of the anti-ageing protein Klotho in vascular physiology and pathophysiology. Ageing Res Rev. 2017)(Donate-Correa J, Klotho in cardiovascular disease: Current and future perspectives. World J Biol Chem. 2015).

At central nervous system level, α Klotho plays an essential role in promoting cognitive abilities and in contrasting neurological and psychiatric disorders (Vo H T., Klotho, the Key to Healthy Brain Aging? Brain Plast. 2018). In animal models, the increased expression of this protein has displayed a cognitive improvement and greater resistance to Alzheimer-related neurodegeneration. Furthermore, in in vitro cell cultures, it has been observed that the protein Klotho induces greater resistance to oxidative stress and significant protection from cytotoxicity induced by protein A13 and by glutamate associated with Alzheimer's disease. (Cararo-Lopes M M, The relevance of α-KLOTHO to the central nervous system: Some key questions. Ageing Res Rev. 2017)

The trans-membrane form of α Klotho which acts as a co-receptor of FGF23 (Fibroblast Growth Factor-23), is constituted of 130 kDa, whereas the secreted forms that can be detected in serum, urine and cerebrospinal fluid can form both due to cleavage of the transmembrane protein and due to alternative splicing (forming the isoform of 70 kDa). In the renal tubule, the membrane protein Klotho regulates the reabsorption of phosphate and controls the metabolism of vitamin D, involved in the homeostasis of calcium. The secreted forms, instead, act independently from the FGF23 receptor and are diffused with hormonal action along the blood stream, regulating the transduction of the insulin signal (Schmid C., Growth hormone and Klotho. J Endocrinol. 2013) and the transduction route of Wnt with anti-oxidizing and anti-ageing effect.

Transgenic mice without Klotho develop a syndrome similar to accelerated ageing, with premature death, osteoporosis, blindness, arteriosclerosis and vascular calcifications, in particular they display a defect in endothelium-dependent vasodilation and in angiogenesis. The protection by the protein Klotho of the cardiovascular system takes place by means of controlling the release of nitric oxide, a known anti-oxidant molecule that contrasts vasoconstriction and endothelial dysfunction. Unlike knock-out mice, mice which hyper-express Klotho live longer than normal mice.

In relation to β Klotho, it is known that it controls the metabolism of lipids, the homeostasis of glucose and the release of bile (Xu Y. Molecular basis of Klotho: from gene to function in aging. Endocr Rev. 2015; Yamamoto M, et al. Regulation of oxidative stress by the anti-aging hormone klotho. J Biol Chem 2005; Ito S., Impaired negative feedback suppression of bile acid synthesis in mice lacking beta Klotho. J Clin Invest 2005; Razzaque M S. The role of Klotho in energy metabolism. Nat Rev Endocrinol 2012). The deregulation of β is connected with alterations to the adipose tissue (Nies V J, Fibroblast Growth Factor Signaling in Metabolic Regulation. Front Endocrinol (Lausanne). 2016) such as obesity. The existence of interaction (cross-talk) between brown adipose tissue, liver and gut microbiota regulated by β Klotho has been noted (E. Somm et al., β-Klotho deficiency protects against obesity through a cross-talk between liver, microbiota, and brown adipose tissue, JCI Insight. 2017). The functions of γKlotho are not very well known and highly debated. (Kim J H., Biological role of anti-aging protein Klotho. J Lifestyle Med 2015). It is known that in a healthy individual the average serum values of Klotho are around 472 pg/ml (Pedersen L, Soluble serum Klotho levels in healthy subjects. Clin Biochem. 2013), whereas the values drop greatly with increasing age, in patients with chronic kidney disease, in subjects affected by cardiovascular diseases or diabetes. In particular, it has been observed that the levels of soluble Klotho are inversely related to serum creatinine. There is still much debate as to the influence of the female/male gender on normal levels of plasma Klotho (Yamazaki Y, Establishment of sandwich ELISA for soluble alpha-Klotho measurement Age-dependent change of soluble alpha-Klotho levels in healthy subjects. Biochem Biophys Res Commun. 2010).

Different studies have tested factors that can increase the release of Klotho and have led to the identification of drugs, natural compounds or lifestyles to be adopted. These include for example ACE inhibitors (ramipril) (Zanchi C, Renal expression of FGF23 in progressive renal disease of diabetes and the effect of ACE inhibitor. PLoS One. 2013) administered intravenously in an animal model of diabetes or diabetic nephropathy (Eltablawy N, Vitamin D protection from rat diabetic nephropathy is partly mediated through Klotho expression and renin-angiotensin inhibition. Arch Physiol Biochem. 2018) the probiotic factors such as *Lactobacillus acidophilus* or *Bifidobacterium bifidum* evaluated as a dietary supplement in an aging mouse model (Kaushal D, Probiotic Dahi containing *Lactobacillus acidophilus* and *Bifidobacterium bifidum* alleviates age-inflicted oxidative stress and improves expression of biomarkers of ageing in mice. Mol Biol Rep. 2012), insulin (Chen C D, Insulin stimulates the cleavage and release of the extracellular domain of Klotho by ADAM10 and ADAM17. Proc Nati Acad Sci USA. 2007) whose effect was analyzed in vitro on monkey kidney cells.

Some compounds, such as activated carbon able to act by sequestrating uremic toxins, such as for example indoxyl sulphate, which reduce the release of klotho have demonstrated effectiveness in different studies (Lekawanvijit S, Chronic kidney disease-induced cardiac fibrosis is ameliorated by reducing circulating levels of a non-dialysable uremic toxin, indoxyl sulphate. PLoS One. 2012).

Finally, contrasting results were obtained from the dietary supplementation of vitamin D, especially in dialyzed patients (Prié D, Reciprocal control of 1,25-dihydroxyvitamin D and FGF23 formation involving the FGF23/Klotho system. Clin J Am Soc Nephrol. 2010; Seibert E, Influence of cholecalciferol supplementation in hemodialysis patients on monocyte subsets: a randomized, double-blind, placebo-controlled clinical trial. Nephron Clin Pract. 2013).

Physical exercise was shown to be one of the main factors able to stably increase circulating Klotho levels. (Avin K G, Skeletal muscle as a regulator of the longevity protein, Klotho. Front Physiol. 2014).

International patent application no. WO2018098375 describes klotho recombinant proteins.

Korean patent application no. KR20170111384 describes compositions comprising klotho for reducing toxicity at renal level induced by the drug tacrolimus.

Chinese patent application no. CN107438423 describes compositions containing klotho for activating the longevity gene.

Canadian patent application no. CA3025461 describes various therapeutic applications of the protein klotho.

US patent application no. US2018289306 describes the use of klotho as a biomarker for kidney damage.

US patent application no. US2018037868 describes genetically modified mesenchymal stem cells expressing klotho.

Chinese patent application no. CN105838661 describes the use of genetic modifications of the gene for hetero transplants of the kidney.

Israeli patent application no. IL201880 and US patent applications no. US2012172314 and US2012232024 describe pharmaceutical preparations containing klotho for treating cancer.

Japanese patent application no. JP2001072607 describes a pharmaceutical composition comprising the vector containing the gene KL which codifies for the protein αklotho which can protect the endothelium from hypertension and atherosclerosis.

Chinese patent no. CN104826164 describes an artificial blood vessel that contains the protein Klotho or GDNF.

Chinese patent applications no. CN102961739, CN107148215, CN106342787, CN106035316 and US patent applications no. US2018070582, US2017265456, US2016302406; Singaporean patent application no. SG10201709595, and Japanese patent applications JP2017186295, JP2017061531, JP2017057184; international patent application no. WO2015152429 describe solutions for the preservation of organs for transplanting.

International patent application publication no. WO02/102149 describes a solution for the preservation, maintenance and perfusion of organs waiting for transplant, comprising: a balanced isotonic solution of potassium, monoacid phosphate, bi-acid phosphate, ions, chloride, sodium and bicarbonate; 50-250 mM of glucose; 0.2-20 mM of alcanoyl L-carnitine or a physiologically acceptable salt thereof; 1-100 mM of L-carnitine or a physiologically acceptable salt thereof; and (e) water, wherein carnitine is preferably present as a citrate salt. The solution can further contain an antioxidant such as mannitol.

US patent application publication no. US2018070582 describes a solution for the preservation of organs comprising: a colloid such as a dextran or polyethylene glycol; buffer compounds with pH buffer properties such as sodium citrate, a component with waterproof proprieties such as mannitol, at least one vitamin, at least one electrolyte, at least one component of the energy provision system, at least one substrate for the formation of antioxidants, one or more amino acids, such as carnitine. In particular, it describes two standard HTK preservation compositions which comprises mannitol and ES2, which comprises sodium citrate, carnitine and a waterproofing agent selected from raffinose, trehalose and lactobionic acid.

The scientific publication Mark D Kay et al., "Normo-thermicHypothermicFlush Using a Novel Phosphate-Free Preservation Solution (AQIX) in Porcine Kidneys", Journal of Surgical Research, 171(1) 275-282, describes the organ solutions called AQIX, Hyperosmolar Citrate (HOC) and University of Wisconsin (UW).

The scientific publication Ren Hany Tolba, "Improved Preservation of Warm Ischemia-Damaged Porcine Kidneys after Cold Storage in Ecosol, a Novel Preservation Solution", Annals Of Transplantation, 20, 233-242, compares two preservation solutions: Ecosol comprising carnitine citrate and HTK comprising mannitol.

Chinese patent no. CN 109 549 032 describes a functional weight loss beverage that comprises malachite tea 16-20%, L-carnitine 8-20%, resistant dextrin 1-3%, sweetener 8-10%, concentrated sweet orange juice 3-5%, citric acid 0.02-0.04%, malic acid 0.02-0.04%, a multivitamin, wherein B1 is 0.002-0.004% 0, B6 is 0.0008% 0-0.0016% 0 and B12 is 0.00008% 0-0.0002% 0 wherein the sweetener is a polyol such as xylitol, maltitol, sorbitol, mannitol and lactitol.

TECHNICAL PROBLEM

The renal tubule cell constitutes the main source for the release of Klotho, which exercises numerous beneficial anti-senescence, anti-fibrotic and anti-inflammatory actions on different body districts.

In conditions of damage or cell ageing, the kidney tubule significantly reduces the production of Klotho which can no longer exercise its essential anti-ageing functions.

Because of its function as a blood filter, the kidney constitutes the organ appointed for the purification of the organism and therefore is exposed to potential damage due to the substances that cross it Among the most harmful exogenous substances for renal physiology there are some drugs and/or metabolites thereof, contrast media used in radiology and antibiotics.

The inventors of the present invention have identified and tested the substances able to protect the production in the epithelial cells of the kidney of the protein Klotho, preventing the suppression of the synthesis and release thereof; this protection is exerted towards different toxic tubule substances such as nephrotoxic substances, agents that cause oxidative stress and iodinated contrast media.

Other conditions such as sepsis or surgical operations such as kidney transplants can drastically and suddenly reduce kidney function leading to a serious pathological condition connected with high mortality rates, defined as acute kidney damage.

Sepsis represents a clinical syndrome characterized by systemic inflammation due to an aberrant immune response of the organism that can evolve into acute kidney damage. It has been demonstrated that the drastic deregulation of Klotho during the course of sepsis determines an increase in the incidence of multi-organ dysfunction and mortality (Jorge L B, Klotho deficiency aggravates sepsis-related multiple organ dysfunction. Am J Physiol Renal Physiol. 2019; Jou-Valencia D, Renal Klotho is Reduced in Septic Patients and Pretreatment With Recombinant Klotho Attenuates Organ Injury in Lipopolysaccharide-Challenged Mice. Crit Care Med. 2018).

To date, kidney transplants represent the elected therapeutic strategy for patients affected by terminal kidney disease offering better quality of life with respect to dialysis. However, there are still numerous cases of late transplant failure mainly due to inevitable events during the donation and transplant procedure such as ischemic damage/reperfusion and due to the poor quality of the organs used.

In fact, the shortage of living donations forces the transplant community to consider as potential candidates for transplants donors after brain death or cardiac death and more recently to extend the enrolment criteria also considering marginal donors (Expanded Criteria Donors): the elderly, those with hypertension, with cardiovascular complications or with serum creatinine greater than 1.5 mg/ml).

In the face of these conditions, characterized by complex physiopathologies that comprise haemodynamic alterations, pro-inflammatory responses and oxidative stress, the present invention provides compounds able to increase the renal production of Klotho which lead to improvements in the kidney function parameters or the quality of the organ to be transplanted.

The aforesaid technical problem is solved by providing a composition consisting of natural substances produced endogenously by the organism and that are involved in normal cell metabolism.

The inventors of the present invention have also performed a purposive selection of the concentration intervals of the individual components including all those available in the state of the art in order to verify and obtain an unexpected and surprising synergistic effect of the components in combination, in which the components in combination show a greater and synergistic effect with respect to the additive effect exercised by the individual components.

SUMMARY

The aforesaid technical problem is solved by providing a pharmaceutical composition comprising in combination as active ingredients citrate and carnitine and appropriate pharmacologically acceptable excipients.

Further subject matter of the present invention is constituted by a pharmaceutical composition comprising in combination as active ingredients citrate, carnitine and optionally and furthermore at least one polyol and appropriate pharmacologically acceptable excipients.

Further subject matter of the present invention is a pharmaceutical composition in liquid form comprising in combination as active ingredients citrate and carnitine and optionally and furthermore at least one polyol added to a preservation and/or conservation solution for organs for transplanting or a perfusion and/or reperfusion solution for organs for transplanting.

The subject matter of the present invention is comprised of the aforesaid compositions for use for reducing the kidney damage induced by nephrotoxic substances.

The subject matter of the present invention is constituted by the aforesaid compositions in liquid form for use as an infusion solution for preventing and/or reducing kidney damage induced by nephrotoxic substances.

The subject matter of the present invention is constituted by the aforesaid compositions in liquid form for use as a preservation and/or conservation solution for organs for transplant and for use as a perfusion and/or reperfusion solution for organs for transplant.

The subject matter of the present invention is further constituted by a solid for of the aforesaid compositions constituting a dietary/nutraceutical product for preventing and/or reducing kidney damage induced by nephrotoxic substances.

Further characteristics of the present invention will become clear from the following detailed description with reference to the appended figures and the experimental data provided.

DETAILED DESCRIPTION OF THE PREFERRED EMBODIMENTS

Figure 1:
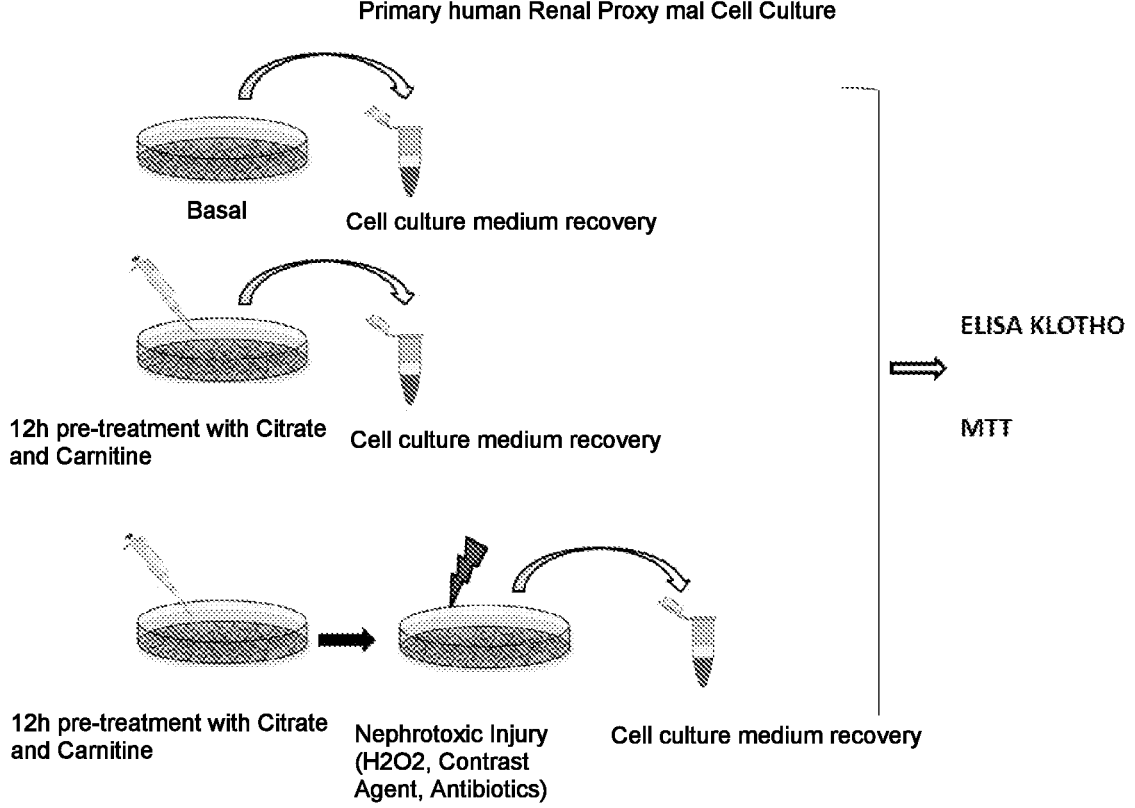
FIG. 1 shows the diagram of the model of culture in vitro and of the conditions used to test the compounds and concentrations of citrate and carnitine able to increase the levels of Klotho in supernatants of RPTEC (renal tubule cells) both in physiological basal conditions and following a nephrotoxic insult.

The present invention relates to a pharmaceutical composition comprising in combination as active ingredients citrate and carnitine and appropriate pharmacologically acceptable excipients.

Alternatively, the pharmaceutical composition comprising in combination as active ingredients carnitine and appropriate pharmacologically acceptable excipients can further comprise at least one polyol.

Preferably the polyol is selected in the group consisting of Erythritol, Sorbitol, Mannitol, Maltitol, Isomalt, Lactitol, polyglycidol, Xylitol.

The pharmaceutical composition can be formulated in liquid or solid form based on the applications.

The solid form may be tablets, pills, rigid capsules, powders, granulates, suppositories.

The present invention relates to a pharmaceutical composition comprising in combination as active ingredients citrate and carnitine and appropriate pharmacologically acceptable excipients able to stimulate the production of the protein Klotho by the renal tubule and endothelial cells.

Preferably, the renal cells are tubule cells and/or endothelial cells.

The present invention relates to a pharmaceutical composition comprising in combination as active ingredients citrate and carnitine and appropriate pharmacologically acceptable excipients, for reducing the kidney damage induced by nephrotoxic substances.

Further subject matter of the present invention is constituted by a composition in liquid form comprising in combination as active ingredients citrate and carnitine and appropriate pharmacologically acceptable excipients for use as a preservation and/or conservation solution for organs for transplanting.

Further subject matter of the present invention is constituted by a composition in liquid form comprising in combination as active ingredients citrate and carnitine and appropriate pharmacologically acceptable excipients for use as a perfusion and/or reperfusion solution for organs for transplanting.

Further subject matter of the present invention is constituted by a composition in liquid form comprising in combination as active ingredients citrate and carnitine and appropriate pharmacologically acceptable excipients for preventing and/or reducing the kidney damage induced by nephrotoxic substances.

Further subject matter of the present invention is constituted by a solid form of the composition comprising in combination as active ingredients citrate and carnitine and appropriate pharmacologically acceptable excipients for constituting a dietary/nutraceutical product for preventing and/or reducing the kidney damage induced by nephrotoxic substances.

The nephrotoxic substances are selected in the group consisting of iodinated contrast media, nephrotoxic antibiotics, anti-inflammatory NSAIDs and agents that induce oxidative stress.

The solid form may preferably be tablets, pills, rigid capsules, powders, granulates, suppositories.

Agents that induce oxidative stress are selected in the group consisting of: oxygen free radicals, oxygen peroxide $(H_2O_2)$, nitrogen reactive species.

Oxygen free radicals (Reactive Oxygen Species, ROS) mean all the intermediate molecules which with subsequent monoelectronic reductions cause the transformation of molecular oxygen into water. For example, the formation of the superoxide anion $(O_2^{*-})$ leads to the release of $H_2O_2$; for example the hydroxyl radical $(HO^-)$ is a highly reactive molecule, it is formed starting from $H_2O_2$ with strong oxidizing capacities and constitutes the agent mainly responsible for the initial phase of peroxidative processes in tissues.

Preferably the reactive oxygen species are selected in the group consisting of: superoxide anion, hydroxyl radical.

Reactive nitrogen species (RNS) are formed when high endocellular levels of superoxide anion and $H_2O$ react with nitric oxide.

Preferably, the reactive nitrogen species are selected in the group consisting of: nitric oxide, peroxynitrite, nitrogen dioxide, nitrogen trioxide.

For example, the dietary/nutraceutical product can be administered before radiological investigations such as for example CT scans, which envisage the use of iodinated contrast media, notoriously nephrotoxic for reducing the renal toxicity effects thereof.

For example, the dietary/neutraceutical product can be administered in combination with nephrotoxic antibiotics or anti-inflammatory NSAIDs for reducing the nephrotoxic effects thereof.

The liquid form of the composition can be administered before radiological investigations such as for example CT scans, which envisage the use of iodinated contrast media, notoriously nephrotoxic for reducing the renal toxicity effects thereof.

The liquid form of the composition can be administered in combination with nephrotoxic antibiotics or anti-inflammatory NSAIDs for reducing the nephrotoxic effects thereof.

The liquid form of the composition can be used as a preservation and/or conservation solution for organs for transplanting.

The liquid form of the composition can be used as a perfusion and/or reperfusion solution for organs for transplanting.

The liquid form of the composition can also be used in the organ pre-collection step in intravenous or arterial infusion.

The compositions in liquid form according to the present invention can be used as solutions for the perfusion of organs for transplanting within perfusion machines.

Sodium citrate is preferably used in the form of sodium disodium citrate, monosodium citrate and trisodium citrate salt.

The citrate is preferably in a concentration comprised between 0.25 and 10 mM.

The citrate is preferably in a concentration comprised between 2.5 mM and 5 mM.

More preferably the citrate is in a concentration equal to 2.5 mM.

More preferably the citrate is in a concentration equal to 5 mM.

The L-carnitine is preferably in a concentration comprised between 2.5 mM and 5 mM.

More preferably the L-carnitine is in a concentration equal to 2.5 mM. More preferably the carnitine is in a concentration equal to 5 mM.

Even more preferably the pharmaceutical composition comprising citrate is in a concentration equal to 5 mM and carnitine in a concentration equal to 5 mM.

The compositions according to the present invention contain, together with the active ingredients at least an appropriate carrier or pharmaceutically acceptable excipient, which may be adjuvants based on the formulation and shape that is to be obtained, which can be selected by a person skilled in the art on the basis of their average knowledge.

The liquid form of the composition may be added to the preservation and/or conservation and/or perfusion and/or reperfusion solutions for organs for transplanting known in the state of the art, which can be suitably selected by a person skilled in the art on the basis of the organ to be preserved, conserved, perfused or reperfused.

Examples of said solutions are described in Guibert E E et al., 2011, Organ Preservation: Current Concepts and New Strategies for the Next Decade, Transfus Med Hemother, 38(2): 125-142 and in O'Callaghan J, Leuvenink H, Friend P, Ploeg R. Kidney Preservation, Chapter 9 in: Kidney Transplantation, Principles and Practice 7th Edition. Saunders. Eds Peter J Morris and Stuart J Knechtle. p 130-141.

For example, the physiological saline solution containing Albumin from human blood and Dextran 40, known by the commercial name STEEN SOLUTION® (XVIVO Perfusion AB, Sweden), generally used for the lung.

Or, for example, the solution containing sodium bicarbonate, potassium phosphate monobasic, potassium phosphate dibasic trihydrate, potassium chloride, known as Euro-collins solution.

Or, for example, the solution containing potassium lactobionate, $KH_2PO_4$, $MgSO_4$, raffinose, adenosine, glutathione, allopurinol, hydroxyethyl starch, known as University of Wisconsin solution or UW solution, Viaspan®, generally used for kidney, liver, pancreas and small intestine.

Or, for example, the solution containing sodium, potassium, magnesium, calcium, ketoglutarate/glutamic acid, histidine, mannitol and tryptophan, known as histidine-tryptophan-ketoglutarate HTK solution.

Or, for example, the solution containing potassium, sodium magnesium, citrate or HEPES, known as Marshall solution or HOC solution.

Or, for example, the solution containing glutathione, mannitol, lactobionic acid, glutamic acid, sodium hydroxide, calcium chloride dihydrate, potassium chloride, magnesium chloride hexahydrate, histidine known as Celsior solution.

Or, for example, the solution containing potassium ions, sodium ions, magnesium ions, sulphate ions, diphosphate, raffinose, lactobionic acid, polyethylene glycol, glutathione, allopurinol, adenosine, known as Institute Georges Lopez Solution or IGL solution.

EXAMPLES

In an in vitro model, renal primary tubule epithelial cells (RPTEC) were placed in culture and subjected to exposure to different solutions containing sodium citrate salt (Trisodium citrate) and L-Carnitine. The concentration intervals tested were: 0.1-50 mM for sodium citrate and 0.1-20 mM for L-Carnitine.

The in vitro model that enabled the testing of the compounds and the concentrations of citrate and carnitine able to increase the levels of Klotho in supernatants of RPTEC both in physiological basal conditions and following a nephrotoxic insult is shown schematically in FIG. 1.

Figure 2:
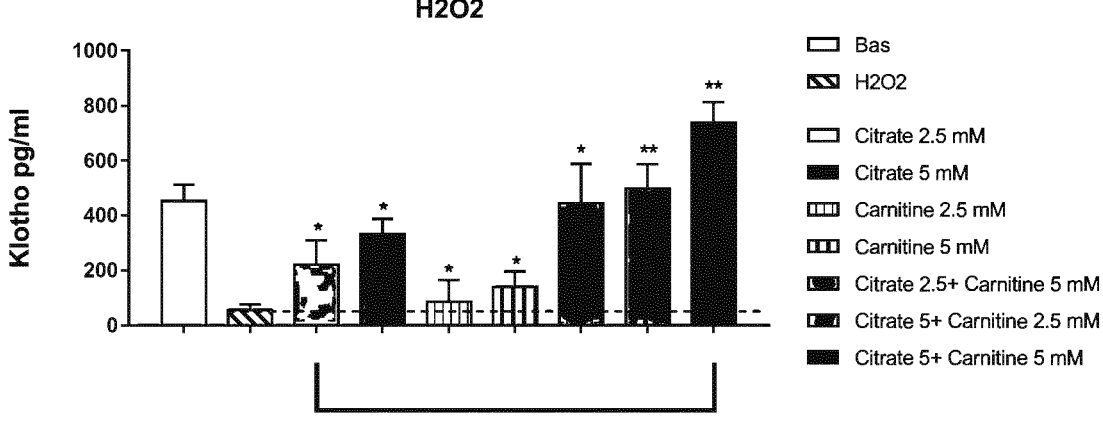
FIG. 2 shows the results related to the release of αKlotho in the supernatant of primary tubule cells after 12 hours of pre-treatment with citrate and/or carnitine and followed by 6 hours of exposure to oxidative stress through stimulation with $H_2O_2$.

The results demonstrate an increase in the release of αKlotho in the supernatant of primary tubule cell cultures after 12 hours of exposure at concentrations of 5 mM of sodium citrate and L-carnitine, as shown in FIG. 2.

Figure 3:
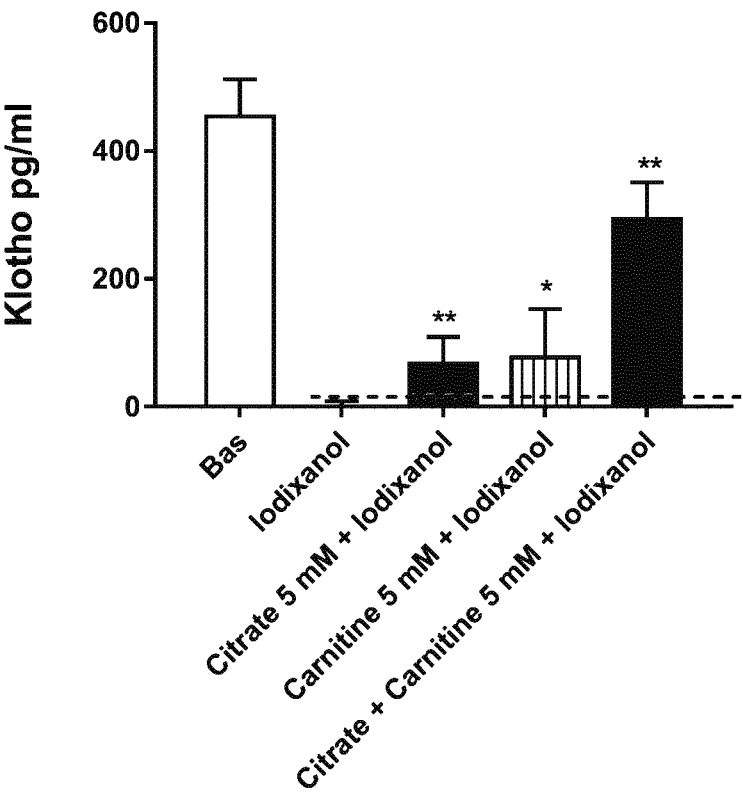
FIG. 3 shows the results related to the release of αKlotho in the supernatant of primary tubule cells after 12 hours of pre-treatment with citrate and/or carnitine and followed by 6 hours of exposure to Iodixanol (commercial name Visipaque, an iodinated contrast medium).
Figure 4:
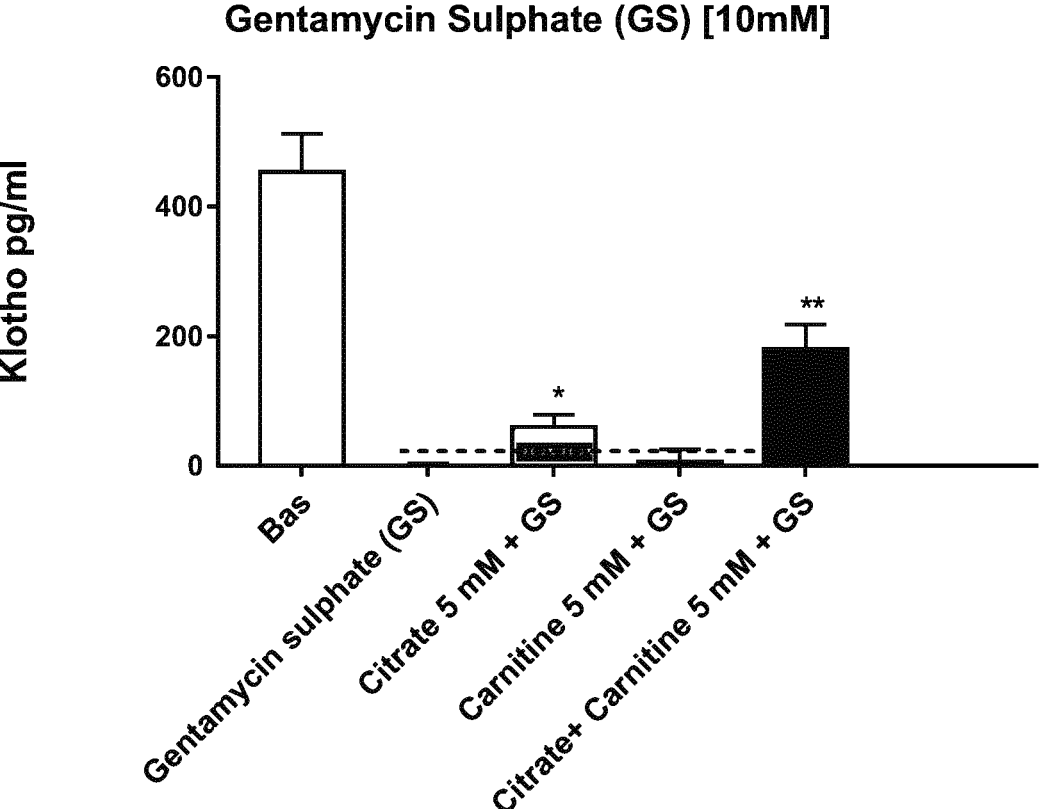
FIG. 4 shows the results related to the release of αKlotho in the supernatant of primary tubule cell cultures after 12 h of pre-treatment with citrate and/or carnitine and followed by 6 h of exposure to tubule damage induced by gentamicin sulphate (antibiotic).

It was then verified whether this increase had also been conserved following different nephrotoxic insults such as the oxidative stress induced by $H_2O_2$, as shown in FIG. 2, exposure to iodinated contrast media, as shown in FIG. 3, to nephrotoxic antibiotics, such as gentamicin sulphate, as shown in FIG. 4.

FIG. 2 shows a graph of the increase in the release of αKlotho in the supernatant of primary tubule cell cultures after 12 hours of pre-treatment with citrate and/or carnitine and followed by 6 hours of exposure to oxidative stress through stimulation with $H_2O_2$ at a concentration of 0.1 mM i.e. the lowest concentration able to induce a statistically significant reduction in Klotho. Concentrations of $H_2O_2$ equal to 0.1, 0.2, 0.5 up to 1 mM were also tested.

The P-value of 5 independent experiments was calculated through t-test (unpaired) and the P value<0.05 and **P value<0.01 were calculated with respect to the condition with $H_2O_2$, as indicated in the figure by the broken line. The soluble aKlotho analysis was performed using the commercial test ELISA lbl code 277789 following the manufacturer's instructions.

The Klotho values (pg/m) for the related conditions indicated are shown in Table 1 below:

TABLE 1

| Conditions | Average Klotho value (pg/ml) |
|---|---|
| $H_2O_2$ 6 h | 55.42 |
| Pretreatment 12 h Citrate 5 mM + 6 h $H_2O_2$ | 333.584 |
| Pretreatment 12 h Carnitine 5 mM + 6 h $H_2O_2$ | 140.25 |
| Pretreatment 12 h Citrate 5 mM + Carnitine 5 mM + 6 h $H_2O_2$ | 739.594 |

Simultaneous exposure to citrate and carnitine provides a synergistic effect, i.e. the combined effect of the two substances is greater than the sum of the increases in citrate or carnitine considered individually, as is highlighted by the numerical values in Table 1.

FIG. 3 shows the results related to the release of αKlotho in the supernatant of primary tubule cells after 12 hours of pre-treatment with citrate and/or carnitine and followed by 6 hours of exposure to the iodinated contrast medium Iodixanol (commercial name Visipaque).

The concentrations of the contrast medium used were 50 and 100 mg/ml; the figure shows the data related to higher concentrations than 100 mg/ml. *P value<0.05; **P value<0.01 compared to the condition with Iodixanol contrast medium only, as indicated by the broken line. Iodixanol induces a drastic reduction in Klotho compared to the basal condition.

The Klotho values (pg/ml) for the related conditions are shown in Table 2 below

TABLE 2

| Conditions | Average Klotho value (pg/ml) |
|---|---|
| Iodixanol 100 mg/ml 6 h | 0 |
| Pre-treatment 12 h Citrate 5 mM + 6 h Iodixanol | 67.79 |
| Pre-treatment 12 h Carnitine 5 mM + 6 h Iodixanol | 77.06 |
| Pre-treatment 12 h Citrate 5 mM + Carnitine 5 mM + 6 h Iodixanol | 294.12 |

Simultaneous exposure to citrate and carnitine provide a synergistic effect, i.e. the combined effect of the two substances is greater than the sum of the increases in citrate or carnitine considered individually, in the presence of Iodixanol, as shown by the numerical values in Table 2.

FIG. 4 shows the results related to the release of αKlotho in the supernatant of primary tubule cells after 12 hours of pre-treatment with citrate and/or carnitine and followed by 6 hours of exposure to the nephrotoxic antibiotic gentamicin sulphate.

Tested concentrations from 0.1-1-10 mM, on the graph the concentration of 10 mM is indicated. *P value<0.05; **P value<0.01 compared to the condition with gentamicin sulphate only, as indicated by the broken line. The increase in levels of Klotho obtained by the co-incubation of citrate and carnitine is synergistic, as highlighted by the numerical values of Table 3 below.

TABLE 3

| Conditions | Average Klotho value (pg/ml) |
| --- | --- |
| Gentamicin sulphate 10 mM 6 h | 0 |
| Pre-treatment 12 h Citrate 5 mM + 6 h Gentamicin sulphate | 60.24 |
| Pre-treatment 12 h Carnitine 5mM + 6 h Gentamicin sulphate | 6.68 |
| Pre-treatment 12 h Citrate 5 mM + Carnitine 5 mM + 6 h Gentamicin sulphate | 180.87 |

The soluble aKlotho analysis was performed using ELISA lbl test.

Figure 5:
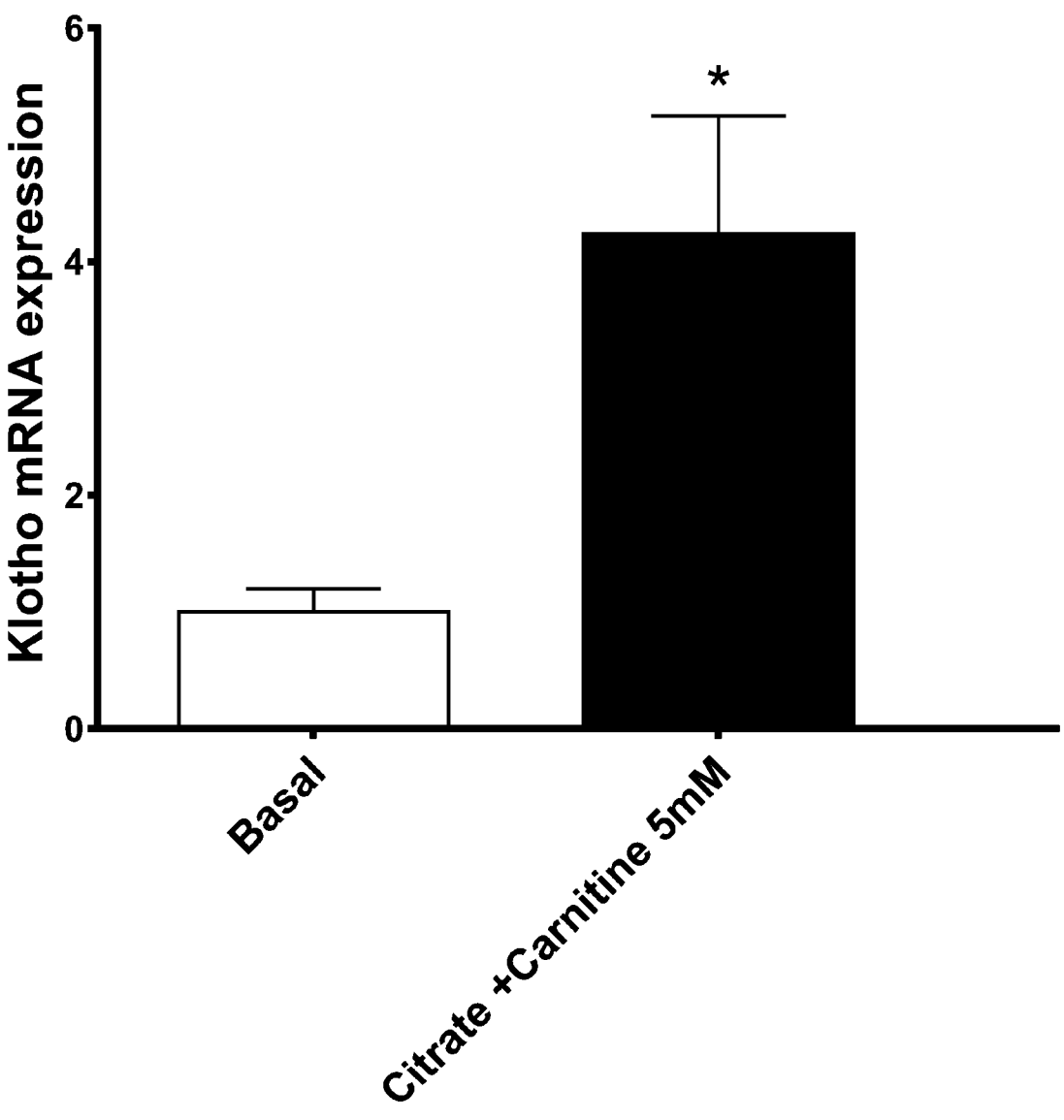
FIG. 5 shows the results related to the Real time PCR performed on cultures of primary endothelial cells deriving from the umbilical cord (HUVEC) for the transcript of the KL gene (αKlotho protein).

The kidney is one of the most vascularized organs in the human body; therefore the effect of the compound on human endothelial cells was tested. FIG. 5 shows a graph of the increase in gene expression levels of KL (codifying the protein αKlotho) by primary endothelial cell cultures (HU-VEC, Human umbilical vein endothelial cells) after 24 hours of exposure to the formulation containing citrate and/or carnitine. Therefore, the compound has no toxic effects on endothelial cells and displays the same ability to induce the transcription of the Klotho gene, as happens in the tubule cells.

The P-value of 3 independent experiments was calculated by means of t-test (unpaired) and the P value (*p<0.05) was calculated with respect to the basal condition. The analysis of the gene expression of the transcript of aKlotho was performed by means of Real time PCR, specifically SYBR green assay (with the SsoAdvanced™ Universal SYBR® Green Supermix) and the quantization was performed by means of the software Light Cycler 96 (Roche) with method $2^{-DDCT}$ assigning value 1 to the basal condition.

Figure 6:
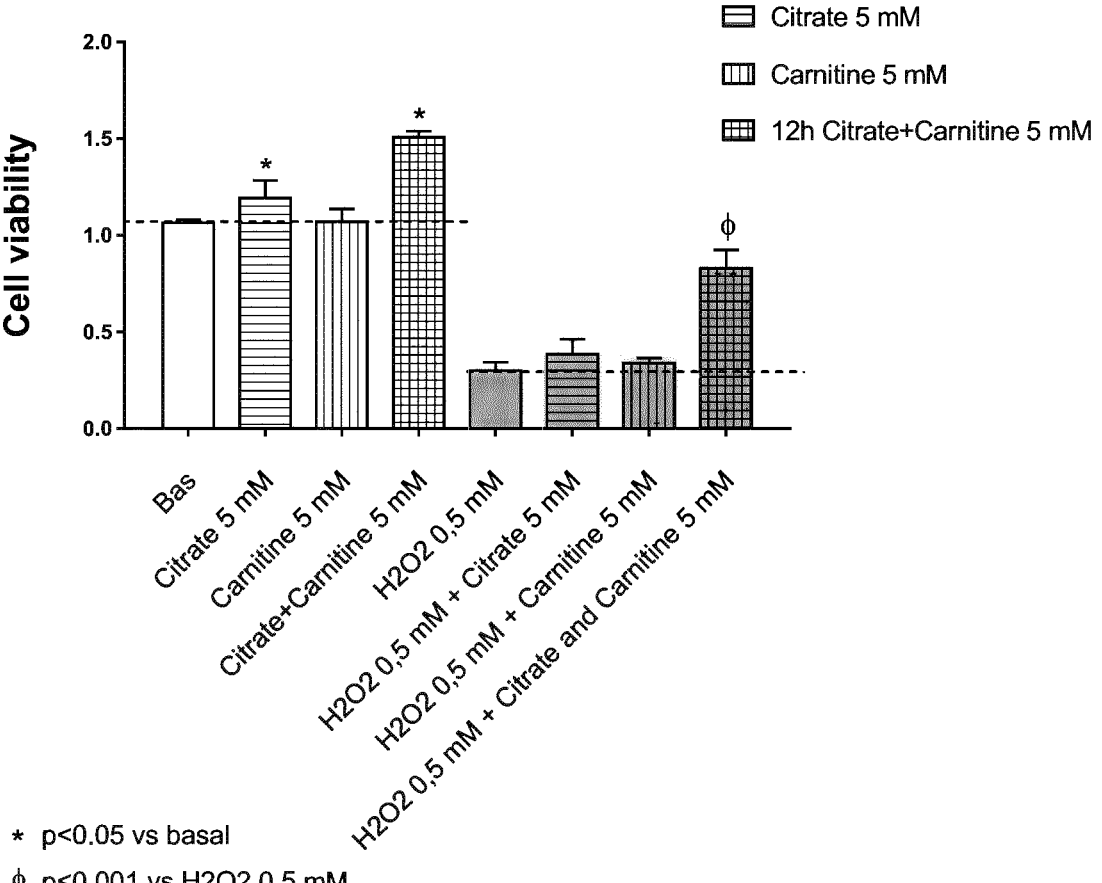
FIG. 6 shows the results of the MTT test, the increase in cell proliferation observed in cultures of primary renal tubule cells after 12 hours of pre-treatment with citrate and/or carnitine at the concentration of 5 mM.

FIG. 6 shows the increase in cell proliferation observed in cultures of primary renal tubule cells after 12 hours of pre-treatment with citrate and/or carnitine at the concentration of 5 mM (bars with white background). The graph also shows the significant reduction in cell viability observed after the exposure of the tubule cells to the cytotoxic concentration of $H_2O_2$ of 0.5 mM (bars with grey background). Only the simultaneous exposure to citrate and carnitine provides the synergistic effect of recovery of cell viability from the oxidative damage induced by $H_2O_2$, i.e. the combined effect of the two substances is greater than the sum of the increases in citrate or carnitine considered individually. Therefore, it is shown that at the concentration of 5 mM, the two substances, present simultaneously and not alone, determine a significant increase in cell viability (MTT test), both under basal conditions and following oxidative stress.

In addition to in vitro experiments, further tests were conducted in two animal models, using the composition citrate 5 mM and carnitine 5 mM.

In a Model of acute kidney injury (AKI) from gentamicin in Zebrafish. The composition, administered in the first five days of life showed no toxicity in vivo. In treated fish, it was capable to protect against AKI with a percentage of more than 60% compared to untreated zebrafish.

Next, a Model of AKI in rats subjected to Ischemia/ Reperfusion damage was used. As previously, the administration of the composition was well tolerated in normal rats without any toxic effect detectable. Interestingly, in mice treated with the compound and subjected to AKI, the composition manages to protect against I/R damage by maintaining renal function at about 88% of healthy control. On the contrary, the untreated rats exhibited a reduction in renal function to 44% from baseline.

The invention claimed is:

1. A liquid pharmaceutical composition comprising:
(a) active ingredients citrate and carnitine; and
(b) a pharmacologically acceptable excipient,
wherein the citrate is at a concentration of about 5 mM in the liquid, and the carnitine is at a concentration of between 2.5 mM and 5 mM in the liquid,
wherein the citrate and carnitine are formulated with:
(i) sodium bicarbonate, potassium phosphate monobasic, potassium phosphate dibasic trihydrate and potassium chloride;
(ii) potassium lactobionate, $KH_2PO_4$, $MgSO_4$, raffinose, adenosine, glutathione, allopurinol and hydroxyethyl starch;
(iii) sodium, potassium, magnesium, calcium, ketoglutarate/glutamic acid, histidine, mannitol and tryptophan; or
(iv) glutathione, mannitol, lactobionic acid, glutamic acid, sodium hydroxide, calcium chloride dihydrate, potassium chloride, magnesium chloride hexahydrate and histidine.

2. The liquid pharmaceutical composition according to claim 1 wherein the carnitine is at a concentration of about 5 mM in the liquid.

3. The liquid pharmaceutical composition according to claim 1 wherein the citrate is at a concentration of 5 mM in the liquid, and the carnitine in a concentration of 5 mM in the liquid.

4. The liquid pharmaceutical composition according to claim 1 further comprising at least one polyol.

5. The liquid pharmaceutical composition according to claim 4 wherein the polyol is selected in the group consisting of Erythritol, Sorbitol, Xylitol, Mannitol, Maltitol, Isomalt, Lactitol, and polyglycidol.

6. The liquid pharmaceutical composition according to claim 1, wherein the citrate comprises a sodium citrate.

7. The liquid pharmaceutical composition according to claim 1 formulated in as a physiological saline solution.

8. The liquid pharmaceutical composition according to claim 7, wherein the physiological saline solution further comprises an albumin.

9. The liquid pharmaceutical composition of claim 7, formulated with a preservation solution, a conservation solution, a perfusion solution and/or a reperfusion solution.

10. The liquid pharmaceutical composition of claim 9, wherein the preservation solution, conservation solution, perfusion solution and/or reperfusion solution comprises a solution selected from the group consisting of: Euro-Collins solution, University of Wisconsin solution, histidine-tryptophan-ketoglutarate solution, Marshall solution, and Institute Georges Lopez solution.

11. The liquid pharmaceutical composition of claim 7, formulated for use as a preservation solution and/or a conservation solution for an organ transplant.

12. The liquid pharmaceutical composition of claim 7, formulated as a perfusion solution and/or a reperfusion solution for an organ transplant.

13. The liquid pharmaceutical composition of claim 1, wherein the citrate and carnitine are formulated with a combination of compounds consisting of: sodium bicarbonate, potassium phosphate monobasic, potassium phosphate dibasic trihydrate and potassium chloride.

14. The liquid pharmaceutical composition of claim 1, wherein the citrate and carnitine are formulated with a combination of compounds consisting of: potassium lactobionate, $KH_2PO_4$, $MgSO_4$, raffinose, adenosine, glutathione, allopurinol and hydroxyethyl starch.

15. The liquid pharmaceutical composition of claim 1, wherein the citrate and carnitine are formulated with a combination of compounds consisting of: sodium, potassium, magnesium, calcium, ketoglutarate/glutamic acid, histidine, mannitol and tryptophan.

16. The liquid pharmaceutical composition of claim 1, wherein the citrate and carnitine are formulated with a combination of compounds consisting of: glutathione, mannitol, lactobionic acid, glutamic acid, sodium hydroxide, calcium chloride dihydrate, potassium chloride, magnesium chloride hexahydrate and histidine.

\* \* \* \* \*